US012790286B2

(12) United States Patent
Bang et al.

(10) Patent No.: US 12,790,286 B2
(45) Date of Patent: Nov. 10, 2026

(54) PROCESS OF RECOVERING 3-HYDROXYPROPIONIC ACID AND SLURRY COMPOSITION COMPRISING 3-HYDROXYPROPIONIC ACID

(71) Applicant: LG CHEM, LTD., Seoul (KR)

(72) Inventors: Yongju Bang, Daejeon (KR); Jeong Eun Kim, Daejeon (KR); Jae Hoon Choe, Daejeon (KR); Donggyun Kang, Daejeon (KR); Woochul Jung, Daejeon (KR); Sang Won Han, Daejeon (KR); Taeho Kim, Daejeon (KR)

(73) Assignee: LG CHEM, LTD., Seoul (KR)

( * ) Notice: Subject to any disclaimer, the term of this patent is extended or adjusted under 35 U.S.C. 154(b) by 404 days.

(21) Appl. No.: 18/569,334

(22) PCT Filed: Nov. 24, 2022

(86) PCT No.: PCT/KR2022/018698
§ 371 (c)(1),
(2) Date: Dec. 12, 2023

(87) PCT Pub. No.: WO2023/096366
PCT Pub. Date: Jun. 1, 2023

(65) Prior Publication Data

US 2024/0286989 A1 Aug. 29, 2024

(30) Foreign Application Priority Data

Nov. 29, 2021 (KR) ........................ 10-2021-0166977
Nov. 29, 2021 (KR) ........................ 10-2021-0167409
Nov. 23, 2022 (KR) ........................ 10-2022-0158661

(51) Int. Cl.

| | |
|---|---|
| ***C07C 51/43*** | (2006.01) |
| ***C07C 59/01*** | (2006.01) |
| ***C12N 9/02*** | (2006.01) |
| ***C12N 9/10*** | (2006.01) |
| ***C12P 7/42*** | (2006.01) |

(52) U.S. Cl.
CPC .............. *C07C 51/43* (2013.01); *C07C 59/01* (2013.01); *C12N 9/0008* (2013.01); *C12N 9/1085* (2013.01); *C12P 7/42* (2013.01); *C12Y 102/01003* (2013.01); *C12Y 205/01017* (2013.01)

(58) Field of Classification Search
CPC ....... C07C 51/43; C07C 59/01; C07C 51/412; C07C 51/02; C12N 9/0008; C12N 9/1085; C12P 7/42; C12P 7/52; C12Y 102/01003; C12Y 205/01017
See application file for complete search history.

(56) References Cited

U.S. PATENT DOCUMENTS

| | | | |
|---|---|---|---|
| 4,444,881 | A | 4/1984 | Urbas |
| 4,739,080 | A | 4/1988 | Sasaki et al. |
| 5,001,245 | A | 3/1991 | Nakano et al. |
| 5,413,901 | A | 5/1995 | Florens et al. |
| 5,453,365 | A | 9/1995 | Sterzel et al. |
| 5,766,439 | A | 6/1998 | Eyal et al. |
| 6,063,958 | A | 5/2000 | Chen et al. |
| 6,747,173 | B2 | 6/2004 | Gerkema et al. |
| 8,883,464 | B2 | 11/2014 | Lynch et al. |
| 9,512,057 | B2 | 12/2016 | Hoppe et al. |
| 10,442,748 | B2 | 10/2019 | Abraham et al. |
| 2008/0193985 | A1 | 8/2008 | Choi et al. |
| 2008/0317934 | A1 | 12/2008 | Hauk et al. |
| 2009/0076297 | A1 | 3/2009 | Bogan, Jr. et al. |
| 2010/0099910 | A1 | 4/2010 | Meng et al. |
| 2011/0098438 | A1 | 4/2011 | Okamoto |
| 2012/0160686 | A1 | 6/2012 | Jump |
| 2013/0071893 | A1 | 3/2013 | Lynch et al. |
| 2013/0122541 | A1 | 5/2013 | Lynch et al. |
| 2014/0045231 | A1 | 2/2014 | Lynch et al. |
| 2015/0056651 | A1 | 2/2015 | Lynch et al. |
| 2015/0344916 | A1 | 12/2015 | Lynch et al. |
| 2016/0031792 | A1 | 2/2016 | Abraham et al. |
| 2016/0060204 | A1 | 3/2016 | Abraham et al. |
| 2016/0348137 | A1 | 12/2016 | Finnegan |
| 2017/0050119 | A1 | 2/2017 | Roa Engel et al. |

(Continued)

FOREIGN PATENT DOCUMENTS

| | | | |
|---|---|---|---|
| CN | 104487584 | B | 5/2018 |
| CN | 110981718 | A | 4/2020 |

(Continued)

OTHER PUBLICATIONS

Urbanus, J. et al., "Intensified crystallization in complex media: Heuristics for crystallization of platform chemicals", Chemical engineering science, vol. 77, pp. 18-25. (Year: 2012).*
PCT Search Report & Written Opinion of PCT/KR2022/019067 issued Mar. 6, 2023, 5 pages.
PCT Search Report of PCT/KR2022/018698 issued on Mar. 8, 2023, 6 pages.
PCT Search Report of PCT/KR2022/019074 issued on Mar. 8, 2023, 5 pages.
PCT Search Report of PCT/KR2022/018943 issued on Mar. 8, 2023, 5 pages.
PCT Search Report of PCT/KR2022/019065 issued on Mar. 6, 2023, 4 pages.

(Continued)

*Primary Examiner* — Deborah D Carr
(74) *Attorney, Agent, or Firm* — ROTHWELL, FIGG, ERNST & MANBECK, P.C.

(57) ABSTRACT

The present invention relates to a process of recovering 3-hydroxypropionic acid, comprising: forming a 3-hydroxypropionate crystal in a concentrate containing 3-hydroxypropionic acid in the presence of an alkali metal salt; preparing a solution containing the 3-hydroxypropionate crystal separated from the concentrate; and adding ammonia to the solution containing the 3-hydroxypropionate crystal, and a slurry composition comprising a precipitate prepared in the process of recovering 3-hydroxypropionic acid, and 3-hydroxypropionic acid.

15 Claims, No Drawings

(56) References Cited

U.S. PATENT DOCUMENTS

| | | | |
|---|---|---|---|
| 2017/0056862 | A1 | 3/2017 | Velasquez et al. |
| 2017/0114377 | A1 | 4/2017 | Lynch et al. |
| 2018/0073044 | A1 | 3/2018 | Visser et al. |
| 2018/0126363 | A1 | 5/2018 | Velasquez et al. |
| 2019/0024125 | A1 | 1/2019 | Kalbasenka et al. |
| 2019/0119708 | A1 | 4/2019 | Lynch et al. |
| 2020/0354728 | A1 | 11/2020 | Shim et al. |
| 2021/0002679 | A1 | 1/2021 | Visser et al. |
| 2021/0009496 | A1 | 1/2021 | Shim et al. |
| 2021/0130856 | A1 | 5/2021 | Kalbasenka et al. |
| 2021/0292267 | A1 | 9/2021 | Shim et al. |
| 2022/0153676 | A1 | 5/2022 | Abraham et al. |
| 2022/0153677 | A1 | 5/2022 | Abraham et al. |
| 2023/0151375 | A1 | 5/2023 | Shim et al. |

FOREIGN PATENT DOCUMENTS

| | | | |
|---|---|---|---|
| EP | 3845486 | A1 | 7/2021 |
| EP | 3885031 | A1 | 9/2021 |
| EP | 4148037 | A1 | 3/2023 |
| JP | H06-099362 | B2 | 12/1994 |
| JP | H07-005600 | B2 | 1/1995 |
| JP | H07-194387 | A | 8/1995 |
| JP | 3015018 | B1 | 2/2000 |
| JP | 2008-502657 | A | 1/2008 |
| JP | 2013-023481 | A | 2/2013 |
| JP | 2013-071898 | A | 4/2013 |
| JP | 5297455 | B2 | 9/2013 |
| JP | 2016-518821 | A | 6/2016 |
| JP | 6271494 | B2 | 1/2018 |
| JP | 6411245 | B2 | 10/2018 |
| JP | 2019-513379 | A | 5/2019 |
| JP | 6574305 | B2 | 9/2019 |
| JP | 2021-502112 | A | 1/2021 |
| JP | 6838968 | B2 | 3/2021 |
| JP | 6890098 | B2 | 6/2021 |
| KR | 10-2008-0003803 | A | 1/2008 |
| KR | 10-2008-0081347 | A | 9/2008 |
| KR | 10-0999425 | B1 | 12/2010 |
| KR | 10-1274369 | B1 | 6/2013 |
| KR | 10-2015-0007155 | A | 1/2015 |
| KR | 10-2018-0036635 | A | 4/2018 |
| KR | 10-2019-0063662 | A | 6/2019 |
| KR | 10-2019-0085439 | A | 7/2019 |
| KR | 10-2019-0115359 | A | 10/2019 |
| KR | 10-2020-0072543 | A | 6/2020 |
| KR | 10-2020-0136490 | A | 12/2020 |
| KR | 10-2021-0012270 | A | 2/2021 |
| KR | 10-2022-0103611 | A | 7/2022 |
| WO | 2015-155535 | A1 | 10/2015 |
| WO | 2015-166098 | A1 | 11/2015 |
| WO | 2016-146721 | A1 | 9/2016 |
| WO | 2020-137974 | A1 | 7/2020 |

OTHER PUBLICATIONS

Urbanus, J. et al., "Intensified crystallization in complex media: Heuristics for crystallization of platform chemicals", Chemical engineering science, 2012, vol. 77, pp. 18-25.

Mcdonald, M. A. et al., "Reactive crystallization: a review", Reaction chemistry & engineering, 2021, vol. 6, pp. 364-400.

Ramachandran, S. et al., "Gluconic acid: properties, applications and microbial production", Food technology & biotechnology, 2006, vol. 44, No. 2, pp. 185-195.

Li, Q.-Z. et al., "Recovery processes of organic acids from fermentation broths in the biomass-based industry", Journal of microbiology and biotechnology, 2016, vol. 26, No. 1, pp. 1-8.

* cited by examiner

PROCESS OF RECOVERING 3-HYDROXYPROPIONIC ACID AND SLURRY COMPOSITION COMPRISING 3-HYDROXYPROPIONIC ACID

CROSS-REFERENCE TO RELATED APPLICATION(S)

This application is a 35 U.S.C. § 371 National Phase Entry Application from PCT/KR2022/018698, filed on Nov. 24, 2022, which claims the benefit of Korean Patent Application No. 10-2021-0166977, filed on Nov. 29, 2021, Korean Patent Application No. 10-2021-0167409, filed on Nov. 29, 2021, and Korean Patent Application No. 10-2022-0158661, filed on Nov. 23, 2022, the disclosures of which are herein incorporated by reference in their entirety.

FIELD OF THE INVENTION

The present invention relates to a process of recovering 3-hydroxypropionic acid and a slurry composition comprising 3-hydroxypropionic acid.

BACKGROUND

3-Hydroxypropionic acid (3HP) is a platform compound that can be converted to various chemicals such as acrylic acid, methyl acrylate, and acrylamide. Since being identified as one of the Top 12 value-added bio-chemicals by the US Department of Energy (DOE) in 2004, it has been actively researched in academic and industrial world.

The production of 3-hydroxypropionic acid is mainly carried out by two methods, chemical and biological, but in the case of chemical method, it has been pointed out that the initial material is expensive and that it is non-environmental because toxic substances are generated during the production process, and thus, environmentally friendly bioprocesses have been attracting attention.

When organic acids are produced by microbial fermentation, other by-products are produced in addition to organic acids such as 3-hydroxypropionic acid in the process of fermenting microorganisms, and thus, a process of extracting and separating organic acids from the fermentation liquor is needed. As methods for extracting and separating organic acids from microbial fermentation liquid, an electrodialysis method, a reverse osmosis membrane method, an organic acid-containing solution-organic solvent reaction extraction method, and the like are used. In particular, the back extraction method using sodium hydroxide (NaOH) is widely used because of its high yield. However, in the case of these methods, since the product is in the form of an organic acid salt, there is a disadvantage that a process for converting it to an organic acid is further needed, and the purity is low. 3-Hydroxypropionic acid exhibits high hydrophilicity and has high solubility and reactivity with water, unlike other organic acids produced through fermentation processes.

This makes it difficult to apply conventional organic acid separation and purification processes such as precipitation and extraction.

The reactive extraction method is a method of extracting an organic acid using an active diluent such as an amine or an alcohol that is highly reactive with the organic acid, which method allows selective extraction of organic acid, and has a relatively high extraction efficiency. Accordingly, an attempt has been made to apply the reaction extraction method even when separating and purifying 3HP. As an example, a method using trioctylamine (TOA) as the amine has been proposed, but there are problems that the extraction efficiency of 3HP is low and a large amount of organic solvent is required. Further, when using tridecylamine as an amine, the extraction efficiency of 3HP is higher than that of TOA, but there is a problem that an emulsion phenomenon occurs in which an organic phase and an aqueous phase are not separated during extraction.

Therefore, there is a need to develop a process of recovering 3-hydroxypropionic acid in a high purity and high yield from a raw material solution containing 3-hydroxypropionic acid, such as a microbial fermentation liquid.

BRIEF SUMMARY

Technical Problem

It is an object of the present invention to provide a process of recovering 3-hydroxypropionic acid in a high yield and high purity by adding ammonia to a solution containing 3-hydroxypropionate crystals, and a slurry composition comprising the precipitate formed in the above process and 3-hydroxypropionic acid.

Technical Solution

Provided herein is a process of recovering 3-hydroxypropionic acid, comprising: forming a 3-hydroxypropionate crystal in a concentrate containing 3-hydroxypropionic acid in the presence of an alkali metal salt; preparing a solution containing the 3-hydroxypropionate crystal separated from the concentrate; and adding ammonia to the solution containing the 3-hydroxypropionate crystal.

Also provided herein is a 3-hydroxypropionic acid-containing slurry composition, comprising a precipitate represented by the following structural formula 4 and 3-hydroxypropionic acid.

$$\text{Cation(OH)}_p \qquad \text{[Structural Formula 4]}$$

the Cation is $Mg^{2+}$ or $Ca^{2+}$, and $Mg^{2+}$ is more preferred.

The p is the number of hydroxide ion ($OH^-$) that bonds to the cation, which is an integer of 1 or more.

DETAILED DESCRIPTION

Now, a process of recovering 3-hydroxypropionic acid and a 3-hydroxypropionic acid-containing slurry composition according to embodiments of the present invention will be described in more detail.

It should be understood that, unless steps included in a preparation method described herein are specified as being sequential or consecutive or otherwise stated, one step and another step included in the preparation method should not be construed as being limited to an order described herein. Therefore, it should be understood that an order of steps included in a preparation method can be changed within the range of understanding of those skilled in the art, and that, in this case, the incidental changes obvious to those skilled in the art fall within the scope of the present invention.

In the present invention, the alkali metal includes both alkali metal and alkali earth metal.

According to one embodiment of the present invention, there can be provided a process of recovering 3-hydroxypropionic acid, comprising: forming a 3-hydroxypropionate crystal in a concentrate containing 3-hydroxypropionic acid in the presence of an alkali metal salt; preparing a solution containing the 3-hydroxypropionate crystal separated from the concentrate; and adding ammonia to the solution containing the 3-hydroxypropionate crystal.

The present inventors have found through experiments that when 3-hydroxypropionic acid is concentrated in the presence of an alkali metal salt to form a 3-hydroxypropionate crystal, and ammonia is added to a solution containing the separated 3-hydroxypropionate crystal, 3-hydroxypropionic acid can be recovered in a high yield and high purity. In addition, when the precipitate produced by adding ammonia is filtered from the slurry and then, the ammonia is stripped from the filtrate to absorb and remove ammonium ions, all nitrogen-containing compounds are also removed, and 3-hydroxypropionic acid can be recovered in a high purity and high yield.

Conventionally, 3-hydroxypropionic acid was recovered by a method using ion-exchange resins, and a gypsum precipitation method. However, the method using ion exchange resins has a problem that a large amount of wastewater is generated, and thus, commercial application is not easy. The gypsum precipitation method has a problem that waste is generated when selling of the gypsum is impossible.

However, the process of recovering 3-hydroxypropionic acid according to one embodiment of the invention can reuse the filtered precipitate as a neutralizing agent. For example, if the 3-hydroxypropionic acid is produced by a biological method through microbial fermentation, the precipitate can be reused as a neutralizing agent in the fermentation process. In addition, the precipitate can be reused as the alkali metal salt in the step of forming a 3-hydroxypropionate crystal from the concentrate containing 3-hydroxypropionic acid. Therefore, the precipitate can be reused during the process without being discarded, thereby suppressing waste generation and realizing an environmentally friendly recovery process.

Further, the recovered ammonia and ammonium ions can be recycled in fields such as fertilizer production, thereby suppressing waste generation and realizing an environmentally friendly 3-hydroxypropionic acid recovery process.

The process of recovering 3-hydroxypropionic acid according to one embodiment of the invention may include adding ammonia to the solution containing 3-hydroxypropionate crystal.

When ammonia is added to the solution containing 3-hydroxypropionate crystal, a slurry composition comprising a precipitate may be formed. For example, when the 3-hydroxypropionate crystal is $Mg(3HP)_2$, a slurry composition including $Mg(OH)_2$ precipitate, the ammonium salt of 3-hydroxypropionic acid, the 3-hydroxypropionic acid 3-hydroxypropionic acid in form of ammonium ions and anions, and the like may be produced as shown in the following Reaction Scheme 1. Further, the $Mg(OH)_2$ precipitate is filtered from this slurry composition, and a greater part of magnesium element (Mg) or magnesium cations can be removed.

$$Mg(3HP)_2 + 2NH_3 + 2H_2O -> Mg(OH)_2 + 2NH_4^+ + 2(3HP^-)$$

Ammonia or ammonia water in which ammonia has been dissolved may be added to the solution containing 3-hydroxypropionate crystal.

Further, the content of ammonia may be 50 parts by weight or more, 70 parts by weight or more, or 100 parts by weight or more, 400 parts by weight or less, 300 parts by weight or less, or 150 parts by weight or less, based on 100 parts by weight of the 3-hydroxypropionate crystal.

If the content of the ammonia is too low, the efficiency of removing cations such as magnesium from the 3-hydroxypropionate crystal may be lowered, and the content of 3-hydroxypropionic acid finally recovered may be low. If the ammonia content is too high, excessive ammonium ions remain in a subsequent process of recovering the 3-hydroxypropionic acid aqueous solution using an adsorbent such as zeolite, and the adsorbent treatment process must be repeated several times, which may result in a decrease in economic efficiency.

The step of adding ammonia to the solution containing 3-hydroxypropionate crystal, a step of stirring after adding the ammonia can be carried out, and the stirring may be carried out at room temperature for 5 hours or more, 10 hours or more, 13 hours or more, or 15 hours or more, and 40 hours or less, 30 hours or less, or 25 hours or less.

In the step of adding ammonia to the solution containing 3-hydroxypropionate crystal, a slurry composition containing a precipitate represented by the following structural formula 3 can be formed.

$$Cation(OH)_p \quad \text{[Structural Formula 3]}$$

In the structural formula 3, the Cation is the cation of the alkali metal salt, and the p is the number of hydroxide ion ($OH^-$) that bonds to the cation, which is an integer of 1 or more.

The cation may be, for example, $Mg^{2+}$ or $Ca^{2+}$, but when it is $Mg^{2+}$, a precipitate can be formed more effectively.

Further, the particle size of the precipitate may be 1.0 μm or more, 1.5 μm or more, 10.0 μm or more, 13.0 μm or more, or 15.0 μm or more, and 300.0 μm or less, 250.0 μm or less, 200.0 μm or less, 150.0 μm or less, 100.0 μm or less, 50.0 μm or less, or 30.0 μm or less. The precipitate satisfies the above-mentioned particle size, and accordingly, filtration separation from the slurry becomes very easy. The precipitate may exhibit various particle shapes such as angular, spherical, plate-shape, and needle-shape. Further, the particle size of the precipitate can be measured by a scanning electron microscopy (SEM). At this time, the particle size of the precipitate may be measured based on the straight-line distance between crystal planes with the longest distance among the straight-line distances between crystal planes contained in the precipitate.

The precipitate can be reused as a neutralizing agent, and for example, when the 3-hydroxypropionic acid is produced by a biological method through microbial fermentation, the precipitate can be reused as a neutralizing agent in the fermentation process. In the step of forming 3-hydroxypropionate crystal in the concentrate containing 3-hydroxypropionic acid, the precipitate can be reused as the alkali metal salt. Therefore, the precipitate can be reused in the process without being discarded, thereby reducing waste generation and realizing an environmentally friendly recovery process.

The process of recovering 3-hydroxypropionic acid according to one embodiment of the invention may include filtering the slurry to recover a filtrate, and stripping ammonia from the filtrate under reduced pressure conditions.

The slurry composition formed through the step of adding ammonia to the solution containing 3-hydroxypropionate crystal contains the precipitate, ammonium salt of 3-hydroxypropionic acid, 3-hydroxypropionic acid in the form of ammonium ions and anions, and the like. As the precipitate is separated and removed by filtering the slurry composition, the filtrate may include the ammonium salt of 3-hydroxypropionic acid, 3-hydroxypropionic acid in form of ammonium ions and anions, and the like. Further, ammonium ions contained in the filtrate may be stripped with ammonia under reduced pressure conditions.

Meanwhile, the filtrate may further include a filtrate after washing and filtering the precipitate.

The reduced pressure condition in which the ammonia is stripped may be 50 mbar or more, 80 mbar or more, 100 mbar or more, or 130 mbar or more, and 400 mbar or less, 300 mbar or less, 250 mbar or less, or 200 mbar or less. As the reduced pressure condition satisfies the above range, ammonia may be stripped from the filtrate.

Further, the temperature conditions in the step of stripping ammonia may be 25° C. or more, 35° C. or more, 45° C. or more, 50° C. or more, 55° C. or more, 60° C. or more, or 65° C. or more, and 80° C. or less, 75° C. or less, or 70° C. or less. Further, the stripping step may be carried out for 30 minutes or more, 40 minutes or more, or 50 minutes or more, or 3 hours or less, or 2 hours or less.

After the step of stripping ammonia is completed, the filtrate from which ammonia has been removed may be recovered by cooling to room temperature.

Meanwhile, the ammonia removed in the step of stripping ammonia can be reused in the step of adding ammonia to the solution containing 3-hydroxypropionate crystal, and can be recycled in fields of fertilizer production or the like. Thereby, in the process of recovering 3-hydroxypropionic acid, the generation of waste can be suppressed, and an environmentally friendly process can be realized.

In the process of recovering 3-hydroxypropionic acid according to one embodiment of the invention, an adsorbent can be added to the filtrate from which ammonia has been removed to adsorb and remove ammonium ions.

As the filtrate from which ammonia has been removed contains 3-hydroxypropionic acid and ammonium ions, ammonium ions can be removed using the adsorbent, thereby recovering 3-hydroxypropionic acid in a high yield and high purity.

The addition amount of the adsorbent may be 10 wt. % or more, 20 wt. % or more, or 30 wt. % or more, and 80 wt. % or less, 70 wt. % or less, or 60 wt. % or less based on 100 wt. % of the filtrate from which ammonia has been removed.

The addition of the adsorbent may be carried out twice or more. When the adsorbent is added twice or more, the amount of the adsorbent added at each stage may satisfy the amount of the adsorbent added. Meanwhile, when the adsorbent is added two times, the ammonium ions are adsorbed and removed by the adsorbent, the adsorbent is removed through filtration, and then the adsorbent is newly added to adsorb and remove the remaining ammonium ions. After that, the adsorbent that has adsorbed ammonium ions is removed through filtration, and finally, 3-hydroxypropionic acid can be recovered in a high yield and high purity.

Meanwhile, the adsorbent may be at least one selected from the group consisting of zeolite, activated carbon, silica gel and alumina gel, and the zeolite can be used as an adsorbent to remove the greater part of the ammonium ions from the filtrate.

Meanwhile, the zeolite from which the ammonium ion has been adsorbed and removed can be converted to a proton-type zeolite through high-temperature heat treatment. Therefore, before being added to the filtrate from which the ammonia has been removed, ammonium ions can be removed from the zeolite through heat treatment, and even after adsorption of ammonium ions, zeolites can be heat-treated to remove ammonium ions. Therefore, since the zeolite can be regenerated through heat treatment, the generation of waste is suppressed, and an environmentally friendly recovery process of 3-hydroxypropionic acid can be realized.

Further, the recovery rate of 3-hydroxypropionic acid by the process of recovering 3-hydroxypropionic acid may be 40% or more, 50% or more, 60% or more, 70% or more, 80% or more, or 90% or more, for example, 40 to 99.9%, 50 to 99.9%, 60 to 99.9%, 70 to 99.9%, 80 to 99.9%, 90 to 99.9%, 40 to 99%, 50 to 99%, 60 to 99%, 70 to 99%, 80 to 99%, 90 to 99%, 40 to 97%, 50 to 97%, 60 to 97%, 70 to 97%, 80 to 97%, 90 to 97%, 40 to 95%, 50 to 95%, 60 to 95%, 70 to 95%, 80 to 95%, or 90 to 95%, but is not limited thereto. The recovery rate may be calculated based on the weight.

Meanwhile, the process of recovering 3-hydroxypropionic acid according to one embodiment of the invention may comprise forming a 3-hydroxypropionate crystal in a concentrate containing 3-hydroxypropionic acid in the presence of an alkali metal salt.

The concentrate containing 3-hydroxypropionic acid may contain 3-hydroxypropionic acid at a concentration of 300 g/L or more, 350 g/L or more, 400 g/L or more, 450 g/L or more, or 500 g/L or more, and may contain 3-hydroxypropionic acid at a concentration of 900 g/L or less, 850 g/L or less, or 800 g/L or less. Whether or not the crystal of 3-hydroxypropionic acid is formed appears to be affected by the presence of an alkali metal salt, the concentration of 3-hydroxypropionic acid in the concentrate, and the like.

Further, when the concentration of the crystal of 3-hydroxypropionic acid in the concentrate is higher than the water solubility of the crystal of 3-hydroxypropionic acid, the crystal of 3-hydroxypropionic acid can be more easily produced.

For example, the water solubility of $Ca(3HP)_2$, which is a crystal of 3-hydroxypropionic acid, is 450 g/L at room temperature, and thus, when the concentration of 3-hydroxypropionic acid in the concentrate exceeds 450 g/L, the formation of $Ca(3HP)_2$ crystal can be promoted. Further, the water solubility of $Mg(3HP)_2$, which is a crystal of 3-hydroxypropionic acid, is 250 g/L at room temperature, and thus, when the concentration of 3-hydroxypropionic acid in the concentrate exceeds 250 g/L, the formation of $Mg(3HP)_2$ crystal can be promoted.

The 3-hydroxypropionate crystal can be formed from a concentrate that satisfies the above-mentioned concentration even while containing the alkali metal salt. The alkali metal salt may be selected without limitation within the purpose range for forming 3-hydroxypropionate crystal. For example, the alkali metal salt may include one or more cations selected from the group consisting of $Mg^{2+}$ and $Ca^{2+}$. Particularly, when a cation of $Mg^{2+}$ or a salt thereof is used, 3-hydroxypropionate crystal can be formed more effectively. For example, the alkali metal salt may be $Ca(OH)_2$, $Mg(OH)_2$ or a mixture thereof.

The alkali metal salt is added and remains in the process of producing the 3-hydroxypropionic acid fermentation liquid, or it can be added in the process of forming the 3-hydroxypropionate crystal in the concentrate containing 300 g/L or more of the 3-hydroxypropionic acid. Further, the concentration of the alkali metal salt may be 10% to 100%, or 30% to 90% of the 3-hydroxypropionic acid concentration, and for example, it can be present in the concentrate at a concentration of 10 to 900 g/L, 50 to 800 g/L, 100 to 700 g/L, or 200 to 600 g/L.

Further, the step of forming a 3-hydroxypropionate crystal of organic acid in the concentrate containing 3-hydroxypropionic acid may further comprise contacting the concentrate of 3-hydroxypropionic acid with a nonsolvent. When contacting the concentrate with the nonsolvent, the 3-hydroxypropionate crystal can be more easily formed. When the concentrate of the formed 3-hydroxypropionic acid is brought into contact with a nonsolvent in the presence of the alkali metal salt, pure 3-hydroxypropionate crystal is formed by controlling the crystal formation rate as compared to crystals formed at a high rate due to overconcentration, and then the crystal size can be increased. The 3-hydroxypropionate crystal contains very low amounts of impurities inside the crystal, and have excellent filterability due to uniform crystal formation, so that not only it is easy to purify, but it is also excellent in shape stability and heating stability in the crystal state, thereby being able to efficiently mass-produce 3-hydroxypropionic acid having high purity.

For example, when a nonsolvent is brought into contact with a concentrate of the formed 3-hydroxypropionic acid in the presence of an alkali metal salt, an alkali metal salt of 3-hydroxypropionic acid is produced, and as the concentration of the produced alkali metal salt of 3-hydroxypropionic acid increases, microcrystals are formed, and solid-liquid phase separation occurs. After that, as crystallization proceeds, the alkali metal salt of 3-hydroxypropionic acid grows into solid crystals (alkali metal salt crystal of 3-hydroxypropionic acid), and the produced 3-hydroxypropionate crystal contain impurities at a very low content while being separated from liquid impurities such as glycerol and 1,3-propanediol. At this time, the nonsolvent serves to promote crystallization of the alkali metal salt of 3-hydroxypropionic acid, so that the solid-liquid separation ability is increased, and the 3-hydroxypropionate crystal having higher purity can be produced.

The volume ratio between the concentrate of 3-hydroxypropionic acid and the nonsolvent may be determined by considering the concentration of 3-hydroxypropionic acid or the volume of the concentrate and nonsolvent. For example, the concentrate and the nonsolvent may be used in a volume ratio of 1:0.5 to 1:20, or 1:0.5 to 1:10, or 1:0.8 to 1:8, or 1:1 to 1:5.

If the volume of the nonsolvent is too small compared to the concentrate, the concentration at which crystals are formed is high, and the rate of crystal formation is increased, so that pure crystal particles are not formed slowly and irregular crystal particles can be rapidly formed. Further, the solid-liquid separation ability is low, which may make it difficult to separate liquid impurities from the alkali metal salt of 3-hydroxypropionic acid to be purified. In addition, if the volume of the nonsolvent is too large compared to the concentrate, the formed crystals may be melted and dissolved in some cases due to the solubility of the nonsolvent, and the time increases in the crystal filtration process after crystal formation, and the amount of waste liquid increases, which may be uneconomical.

The nonsolvent may include an alcohol-based nonsolvent, a ketone-based nonsolvent, a nitrile-based nonsolvent, or a mixture of two or more thereof, and more specifically, at least one alcohol-based nonsolvent may be used.

The ketone-based nonsolvent may include one or more selected from the group consisting of acetone, methyl ethyl ketone, cyclohexanone, diethyl ketone, acetophenone, methyl isobutyl ketone, methylisoamylketone, isophorone and di-(isobutyl)ketone. The alcohol-based nonsolvent may include one or more selected from the group consisting of methanol, ethanol, allyl alcohol, 1-propanol, 2-propanol, 1-butanol, 2-butanol, isobutanol, benzyl alcohol, cyclohexanol, diacetone alcohol, ethylene glycol monoethyl ether, diethylene glycol monomethyl ether, diethylene glycol monoethyl ether, ethylene glycol monobutyl ether, diethylene glycol monobutyl ether, 2-methoxyethanol and 1-decanol. The nitrile-based nonsolvent may include one or more selected from the group consisting of acetonitrile, propionitrile, butyronitrile, valeronitrile, caprylonitrile, heptanenitrile, cyclopentane carbonitrile, cyclohexane carbonitrile, 2-fluorobenzonitrile, 4-fluorobenzonitrile, difluorobenzonitrile, trifluorobenzonitrile, phenylacetonitrile, 2-fluorophenylacetonitrile, and 4-fluorophenylacetonitrile.

The step of contacting the concentrate with a nonsolvent to form a 3-hydroxypropionate crystal may be carried out at a temperature of 0° C. or more, 15° C. or more, 30° C. or more, 35° C. or more, 40° C. or more, 45° C. or more, 50° C. or more, or 55° C. or more, and may be carried out at a temperature of 100° C. or less, 90° C. or less, 80° C. or less, 75° C. or less, 70° C. or less, 65° C. or less, or 0° C. to 100° C.

At this time, the temperature may be adjusted to the above range by adding a non-solvent at the above-described temperature to the concentrate, or by heating or cooling in a state in which the concentrate and the nonsolvent are mixed.

The 3-hydroxypropionate crystal may be the form shown in the following structural formula 1 or structural formula 2. That is, the 3-hydroxypropionate crystal may include 3-hydroxypropionate in the form shown in the structural formula 1 or structural formula 2.

In the structural formula 1 and structural formula 2, Cation means a cation, 3HP means 3-hydroxypropionic acid that binds to the cation, n is the number of 3HP that binds to the cation and means an integer of 1 or more, and in the structural formula 2, m is the number of water molecules that binds to Cation(3HP)n in the hydrate, which is an integer of 1 or more. The cation may be, for example, $Mg^{2+}$ or $Ca^{2+}$, but in the case of $Mg^{2+}$, 3-hydroxypropionate crystal may be formed more effectively.

$\text{Cation(3HP)}_n$ [Structural Formula 1]

$\text{Cation(3HP)}_n\cdot m\text{H}_2\text{O}$ [Structural Formula 2]

Further, the step of forming 3-hydroxypropionate crystal may further include stirring the concentrate.

The stirring step can be carried out at a temperature of 0 to 70 degrees Celsius, 0 to 60 degrees Celsius, 0 to 50 degrees Celsius, 0 to 40 degrees Celsius, 0 to 35 degrees Celsius, 0 to 30 degrees Celsius, 10 to 70 degrees Celsius, 10 to 60 degrees Celsius, 10 to 50 degrees Celsius, 10 to 40 degrees Celsius, 10 to 35 degrees Celsius, 10 to 30 degrees Celsius, 15 to 70 degrees Celsius, 15 to 60 degrees Celsius, 15 to 50 degrees Celsius, 15 to 40 degrees Celsius, 15 to 35 degrees Celsius, 15 to 30 degrees Celsius, 20 to 70 degrees Celsius, 20 to 60 degrees Celsius, 20 to 50 degrees Celsius, 20 to 40 degrees Celsius, 20 to 35 degrees Celsius, or 20 to 30 degrees Celsius (e.g., room temperature), and/or under conditions of 100 to 2000 rpm, 100 to 1500 rpm, 100 to 1000 rpm, 100 to 500 rpm, 100 to 400 rpm, or 200 to 400 rpm (e.g., about 300 rpm).

The particle size distribution $D_{50}$ of the 3-hydroxypropionate crystal may be 20 μm or more and 90 μm or less, 25 μm or more and 85 μm or less, 30 μm or more and 80 μm or less, or 35 μm or more and 75 μm or less.

In addition, the particle size distribution $D_{10}$ of the 3-hydroxypropionate crystal may be 5 μm or more and 40 μm or less, 8 μm or more and 35 μm or less, 10 μm or more and 30 μm or less, and the particle size distribution $D_{90}$ of the 3-hydroxypropionate crystal may be 50 μm or more and 200 μm or less, 60 μm or more and 190 μm or less, 65 μm or more and 180 μm or less, 70 μm or more and 175 μm or less.

The particle size distributions $D_{50}$, $D_{10}$ and $D_{90}$ mean particle diameters at which cumulative volumes of particles reach 50%, 10% and 90%, respectively, in the particle size distribution curve of the particles, wherein the $D_{50}$, $D_{10}$ and $D_{90}$ can be measured using, for example, a laser diffraction method. The laser diffraction method can generally measure particle sizes ranging from a submicron range to several millimeters, and can obtain results with high reproducibility and high resolvability.

If the particle size distributions $D_{50}$, $D_{10}$ and $D_{90}$ of the 3-hydroxypropionate crystal is too large, impurities that must be removed during crystallization may be contained in the crystals, which results in a reduction in purification efficiency. If the particle size distributions are too small, the liquid permeability during filtration of the crystals may be lowered.

Meanwhile, the $(D_{90}-D_{10})/D_{50}$ of the 3-hydroxypropionate crystal may be 1.00 or more and 3.00 or less, 1.20 or more and 2.80 or less, 1.40 or more and 2.60 or less, or 1.60 or more and 2.40 or less.

Further, the 3-hydroxypropionate crystal may have a volume average particle size of 30 μm or more and 100 μm or less, 35 μm or more and 95 μm or less, or 40 μm or more and 90 μm or less, a number average particle size of 1 μm or more and 30 μm or less, 3 μm or more and 25 μm or less, or 5 μm or more and 20 μm or less, and a volume average particle size of 10 μm or more and 70 μm or less, 15 μm or more and 60 μm or less, or 20 μm or more and 55 μm or less.

If the volume average particle size, number average particle size, and volume average particle size of the 3-hydroxypropionate crystal are too large, impurities that must be removed during crystallization may be contained in the crystals, which results in a reduction in purification efficiency. If they are too small, the liquid permeability during filtration of the crystals may be lowered.

Further, the LW ratio (length to width ratio) and average LW ratio in the particle size distribution ($D_{10}$, $D_{50}$, $D_{90}$) of the 3-hydroxypropionate crystal are 0.50 or more and 3.00 or less, 0.70 or more, 2.80 or less, and 1.00 or more and 2.50 or more. If the LW ratio of the 3-hydroxypropionate crystals is too large, problems of fluidity and clogging may occur during transfer of the crystals, and if the LW ratio is too small, the liquid permeability during filtration of the crystals may be lowered.

The 3-hydroxypropionate crystal can measure the moisture content contained in the crystal by the Karl Fischer method, and the moisture content contained in the 3-hydroxypropionate crystal may be 200 ppm or more and 5000 ppm or less, 250 ppm or more and 4800 ppm or less, 300 ppm or more and 4600 ppm or less, or 350 ppm or more and 4400 ppm or less.

At this time, the moisture contained in the 3-hydroxypropionate crystal means the attached moisture contained between the crystals, rather than the crystal moisture (for example, $Ca(3HP)_2 \cdot 2H_2O$). Further, if the moisture content contained in the 3-hydroxypropionate crystal is too high, it may be recovered in the form of a slurry rather than a crystalline solid, or impurities may be contained in the water, which may cause a problem of a decrease in purity improvement.

In the recovery process according to one embodiment of the invention, as 3-hydroxypropionic acid is prepared through a process such as fermenting a bacterium strain having 3-hydroxypropionic acid-producing ability as described below, the 3-hydroxypropionate crystal may contain a radioactive carbon isotope ($^{14}C$).

The radioactive carbon isotope ($^{14}C$) contains about 1 atom per $10^{12}$ carbon atoms in earth's atmosphere and has a half-life of about 5700 years, and carbon stocks can become abundant in the upper atmosphere due to nuclear reactions in which cosmic rays and normal nitrogen ($^{14}N$) participate. Meanwhile, in fossil fuels, isotopes have broken long ago, so that the $^{14}C$ ratio may be substantially zero. When bio-derived raw materials are used as the 3-hydroxypropionic acid raw material, or fossil fuels are used together with it, the content of radioactive carbon isotopes (pMC; percent modern carbon) and the content of bio-carbon contained in 3-hydroxypropionic acid can be measured according to the standard of ASTM D6866-21.

After carbon atoms contained in the compound to be measured is made into graphite form or carbon dioxide gas form, and can be measured, for example, by the mass spectrometer, or can be measured according to liquid scintillation analysis method. At this time, the two radioactive isotopes can be separated using an accelerator for separating $^{14}C$ ions from $^{12}C$ ions together with the mass spectrometer, and the content and the content ratio can be measured by a mass spectrometer.

The 3-hydroxypropionate crystal has a radiocarbon isotope content of 20 pMC (percent modern carbon) or more, 50 pMC or more, 90 pMC or more, 100 pMC or more, and a biocarbon content of 20 wt. % or more, 50 wt. % or more, 80 wt. %, 90 wt. %, or 95 wt. %, as measured according to the standard of ASTM D6866-21.

The radiocarbon isotope ratio (pMC) means the ratio of the radiocarbon isotope ($^{14}C$) contained in the 3-hydroxypropionic acid crystals to the radiocarbon isotope ($^{14}C$) of the modern standard reference material, and it can be greater than 100% because the nuclear test program of the 1950s is still in effect and not extinguished.

Further, the content of biocarbon means the content of biocarbon relative to the total carbon content contained in the 3-hydroxypropionate crystal. As this value is larger, it may correspond to an environmentally friendly compound.

Meanwhile, if the radiocarbon isotope content (pMC) and biocarbon content of the 3-hydroxypropionate crystal are too low, the environmental friendliness is reduced, which may not be seen as a bio-derived material.

The crystalline state of the 3-hydroxypropionate crystal can be confirmed through peaks and the like in an X-ray diffraction (XRD) graph.

For example, the 3-hydroxypropionate crystal may exhibit peaks between crystal lattices in the 2θ value range of 8 to 22° during X-ray diffraction (XRD) analysis.

For example, when the concentrate contains magnesium hydroxide ($Mg(OH)_2$), and the formed 3-hydroxypropionate crystal is $Mg(3HP)_2$, peaks between the crystal lattices due to the bond between 3-hydroxypropionic acid and magnesium may appear in the 2θ value range of 8 to 15° during X-ray diffraction (XRD) analysis for $Mg(3HP)_2$. Such peaks show different results from the X-ray diffraction (XRD) analysis results for magnesium hydroxide ($Mg(OH)_2$) or magnesium sulfate ($Mg(SO_4)$). As a result of the X-ray diffraction (XRD) analysis, it can be confirmed that when a specific peak appears in the 2θ value range of 8 to 15°, $Mg(3HP)_2$ crystal is formed.

Specifically, during X-ray diffraction (XRD) analysis for $Mg(3HP)_2$, 3 or more, 4 or more, or 5 or more peaks may appear in the 2θ value range of 8 to 15°, and for example, peaks may appear in the 2θ value range of 8.2 to 9.3°, 9.5 to 11.0°, 11.2 to 12.7°, 12.9 to 13.3°, and 13.5 to 14.8°, respectively.

Further, when calcium hydroxide ($Ca(OH)_2$) is contained in the concentrate and the 3-hydroxypropionate crystal formed therefrom are $Ca(3HP)_2$, peaks between the crystal lattices due to the bond between 3-hydroxypropionic acid and calcium may appear in the 2θ value range of 10 to 22° during X-ray diffraction (XRD) analysis for $Ca(3HP)_2$. Such peaks show different results from the X-ray diffraction (XRD) analysis results for calcium hydroxide ($Ca(OH)_2$) or calcium sulfate ($Ca(SO_4)$). As a result of the X-ray diffraction (XRD) analysis, it can be confirmed that when a specific peak appears in the 2θ value range of 10 to 22°, $Ca(3HP)_2$ crystal is formed.

Specifically, during X-ray diffraction (XRD) analysis for $Ca(3HP)_2$, 3 or more, 5 or more, 7 or more or 9 or more peaks may appear in the 2θ value range of 10 to 22°, and for example, peaks may appear in the 2θ value range of 10.0 to 11.0°, 11.1 to 11.6°, 11.6 to 12.5°, 12.7 to 13.6°, 13.8 to 16.0°, 17.0 to 18.0°, 19.0 to 19.8°, 20.2 to 21.2°, or 21.5 to 22.0°, respectively.

Meanwhile, the incident angle (θ) means the point at which a first differential value (slope of the tangent line, dy/dx) is 0 on a graph where the horizontal axis (x-axis) in the x-y plane is a value of two times the incident angle (2θ) of the incident X-ray, and the vertical axis (y-axis) in the x-y plane is a diffraction intensity, wherein as the value (2θ) of two times the angle of incidence of the incident X-ray, which is the horizontal axis (x-axis), increases in the positive direction, the first differential value (slope of the tangent line, dy/dx) of two times (2θ) the incident angle of X-rays, which is the horizontal axis (x-axis), with respect to the diffraction intensity, which is the vertical axis (y-axis), changes from a positive value to a negative value.

Further, the 3-hydroxypropionate crystal may have a distance (d value) between atoms in the crystals derived from X-ray diffraction (XRD) analysis of 1.00 Å or more and 15.00 Å or less, 1.50 Å or more and 13.00 Å or less, 2.00 Å or more and 11.00 Å or less, 2.50 Å or more and 10.00 Å or less.

For example, when the 3-hydroxypropionate crystal is $Mg(3HP)_2$, a distance (d value) between atoms in the crystals of the peak appearing in the 2θ value range of 8 to 15° may be 1.00 Å or more and 15.00 Å or less, 2.00 Å or more and 13.00 Å or less, 4.00 Å or more and 11.00 Å or less, 5.50 Å or more and 10.00 Å or less.

Further, when the 3-hydroxypropionate crystal is $Ca(3HP)_2$, the distance (d value) between atoms in the crystals of the peak appearing in the 2θ value range of 10 to 22° may be 1.00 Å or more and 15.00 Å or less, 2.00 Å or more and 13.00 Å or less, 3.00 Å or more and 10.00 Å or less, 3.40 Å or more and 9.00 Å or less, or 4.00 Å or more and 8.50 Å or less.

Further, the 3-hydroxypropionate crystal may have a glass transition temperature of −55° C. or more and −30° C. or less, a melting point of 30° C. or more and 170° C. or less, and a crystallization temperature of 25° C. or more and 170° C. or less.

The glass transition temperature, melting point, and crystallization temperature may be measured by a differential scanning calorimetry (DSC) for the 3-hydroxypropionate crystal, wherein the heating rate during measurement may be 1 to 20° C./min. Further, the 3-hydroxypropionate crystalate may have a glass transition temperature of −55° C. or more and −30° C. or less, −50° C. or more and −35° C. or less, or −45° C. or more and −40° C. or less. Further, the melting point of the 3-hydroxypropionate crystal may be 30° C. or more and 170° C. or less, 31° C. or more and 160° C. or less, 32° C. or more and 150° C. or less. Further, the crystallization temperature of the 3-hydroxypropionate crystal may be 25° C. or more and 170° C. or less, 27° C. or more and 160° C. or less, or 30° C. or more and 150° C. or less. In addition, the crystallization stability section of the 3-hydroxypropionate crystal may be −40° C. to 150° C.

The purity of 3-hydroxypropionate contained in the 3-hydroxypropionate crystal may be calculated as a percentage (%) of the mass of the compound having the structural formula 1 and/or structural formula 2 relative to the mass of the total crystal recovered. For example, the purity of 3-hydroxypropionate contained in the 3-hydroxypropionate crystal may be 70% or more, 80% or more, 90% or more, 70 to 99.9%, 80 to 99.9%, 90 to 99.9%, 70 to 99%, 80 to 99%, or 90 to 99%, but is not limited thereto.

The process of recovering 3-hydroxypropionic acid according to one embodiment of the invention may comprise fermenting a bacterium strain having 3-hydroxypropionic acid-producing ability to produce a 3-hydroxypropionic acid fermentation liquor; and concentrating the fermentation liquid to form the concentrate containing 300 g/L or ore of 3-hydroxypropionic acid, prior to the step of forming the 3-hydroxypropionate crystal.

The bacterium strain having 3-hydroxypropionic acid-producing ability may include genes encoding at least one or two proteins selected from the group consisting of glycerol dehydratase and aldehyde dehydrogenase.

In one example, the 3-hydroxypropionic acid-producing strain may further include a gene (gdrAB) encoding glycerol dehydratase reactivator (GdrAB). In one example, the 3-hydroxypropionic acid-producing strain may be a bacterium strain that is further capable of biosynthesizing vitamin B12.

The glycerol dehydratase may be encoded by dhaB (GenBank accession no. U30903.1) gene, but is not limited thereto. The dhaB gene may be an enzyme derived from *Klebsiella pneumonia*, but is not limited thereto. The gene encoding the glycerol dehydratase may include a gene encoding dhaB1, dhaB2 and/or dhaB3. The glycerol dehydratase protein and the gene encoding it may include mutations in the gene and/or amino acid sequence within the range of maintaining an enzyme activity that decomposes glycerol to 3-hydroxypropanal (3-HPA) and water ($H_2O$).

The gene (aldH) encoding the aldehyde dehydrogenase (ALDH) may be, for example, aldH (GenBank Accession no. U00096.3; EaldH) gene derived from *Escherichia coli* or *E. coli* K12 MG1655 cell line, puuC gene derived from *Klebsiella pneumoniae*, and/or KGSADH gene from Azospirillum brasilense, but is not limited thereto. The aldehyde dehydrogenase protein and the gene encoding it may include mutations in the gene and/or amino acid sequence within the range of maintaining the activity for producing 3-hydroxypropionic acid from 3-hydroxypropanal.

The medium for producing the fermentation liquid can be selected without limitation within the range for the purposes for producing 3-hydroxypropionic acid. In one example, the medium may contain glycerol as a carbon source. In another example, the medium may be crude glycerol and/or pretreated crude glycerol, but is not limited thereto. In one example, the production medium may further include vitamin B12.

In the step of fermenting a bacterium strain having 3-hydroxypropionic acid-producing ability to produce a 3-hydroxypropionic acid fermentation liquor, the concentration of 3-hydroxypropionic acid contained in the 3-hydroxypropionic acid fermentation liquor may be 1 to 200 g/L, 10 to 150 g/L, 30 to 130 g/L, or 40 to 100 g/L.

Further, the fermentation may be a neutral fermentation, for example, it may be maintained in the pH range of 6 to 8, 6.5 to 8, 6 to 7.5, or 6.5 to 7.5 during fermentation, but is not limited thereto. The pH range can be appropriately adjusted as needed. The alkali metal salt may be added for the neutral fermentation. The alkali metal salt may include $Mg^{2+}$, $Ca^{2+}$ or a mixture thereof. Further, the alkali metal salt may be $Ca(OH)_2$ or $Mg(OH)_2$, but is not limited thereto.

The process of recovering 3-hydroxypropionic acid according to one embodiment of the invention may further include removing (separating) cells from the fermentation liquid; purifying and/or decolorizing the fermentation liquid and/or the fermentation liquid from which cells has been removed; and/or filtering the fermentation liquid and/or the fermentation liquid from which cells have been removed, after the step of producing the 3-hydroxypropionic acid fermentation liquid.

Removal (separation) of the cells may be carried out by selecting methods known in the art without limitation within the range of cell (strain) removal purposes. In one example, the separation of the cells may be carried out by centrifugation.

The step of purifying and/or decolorizing the fermentation liquid and/or the fermentation liquid from which cells have been removed can be carried out by selecting methods known in the art without limitation within the range of the purpose of purification of the fermentation liquid. For example, the step can be carried out by mixing activated carbon with the fermentation liquid and then removing the activated carbon, but is not limited thereto.

The step of filtering the fermentation liquid and/or the fermentation liquid from which cells have been removed can be carried out by selecting methods known in the art without limitation within the range of the purposes of removal of solid impurities, removal of proteins and/or materials with hydrophobic functional groups, and/or decoloration. For example, the step can be carried out by filter filtration and/or activated carbon filtration methods, but is not limited thereto.

The process of recovering 3-hydroxypropionic acid according to one embodiment of the invention may comprise concentrating the fermentation liquid to form the concentrate containing 3-hydroxypropionic acid, after the step of fermenting the bacterium strain having 3-hydroxypropionic acid-producing ability to produce a 3-hydroxypropionic acid fermentation liquid.

Concentration of the fermentation liquid may be carried out by evaporating the fermentation liquid (e.g., a liquid component of the fermentation liquid).

The concentration may be carried out by any means commonly available for evaporating the liquid component of the fermentation liquid. For example, the concentration may be carried out by rotary evaporation, evaporation concentration, vacuum concentration, reduced pressure concentration, and the like, but is not limited thereto.

In one example, the concentration of 3-hydroxypropionic acid in the fermentation liquid after concentration may be increased by 2 to 50 times, 2 to 40 times, 2 to 30 times, 2 to 20 times, 2 to 10 times, 5 to 50 times, 5 to 40 times, 5 to 30 times, 5 to 20 times, or 5 to 10 times compared to before concentration.

The process of recovering 3-hydroxypropionic acid according to one embodiment of the invention may comprise preparing a solution containing 3-hydroxypropionate crystal separated from the concentrate, after the step of forming the 3-hydroxypropionate crystal.

As mentioned above, as the 3-hydroxypropionate crystal are produced in the fermentation process, the concentrate in which the fermentation liquid has been concentrated may contain a large amount of impurities such as bacterium strains, carbon sources, and alkali metal salts in addition to the 3-hydroxypropionate crystal. However, in the process of recovering 3-hydroxypropionic acid according to one embodiment of the invention, the impurities can be removed by solid-liquid separation and recovery of 3-hydroxypropionate crystal from the concentrate, and the impurities may not be contained even in a solution prepared by dissolving the separated 3-hydroxypropionic acid crystals in a solvent such as distilled water.

Therefore, when ammonia is added to the concentrate without separating the 3-hydroxypropionic acid crystals from the concentrate, a large amount of impurities are contained in the concentrate, which may make it difficult to finally recover 3-hydroxypropionic acid with a high concentration and high purity.

For example, the 3-hydroxypropionate crystal can be separated from the concentrate using a filtration flask, a vacuum pump, or the like, and the separated 3-hydroxypropionate crystal can be dissolved in a solvent such as distilled water to produce an aqueous solution of 3-hydroxypropionate crystal.

The solution containing 3-hydroxypropionate crystal may contain 3-hydroxypropionate crystal at a concentration of 100 g/L or more, 150 g/L or more, or 200 g/L or more, and may contain it at a concentration of 800 g/L or less, 750 g/L or less, or 700 g/L or less. If the concentration of the 3-hydroxypropionate crystal contained in the solution containing 3-hydroxypropionate crystal is too low, the concentration of 3-hydroxypropionic acid finally recovered may be lowered, and if the concentration of the 3-hydroxypropionate crystal is too high, 3-hydroxypropionic acid may be precipitated, or the solid phase concentration after precipitation may be too high, and thus, the recovery rate may be reduced due to a decrease in fluidity.

According to another embodiment of the present invention, a 3-hydroxypropionic acid-containing slurry composition, comprising a precipitate represented by the following structural formula 4 and 3-hydroxypropionic acid is provided:

$$\text{Cation(OH)}_p \quad \text{[Structural Formula 4]}$$

in the structural formula 4, the Cation is the cation of the alkali metal salt, and for example, it may be $Mg^{2+}$ or $Ca^{2+}$, but in the case of $Mg^{2+}$, the precipitate can be formed more effectively.

Further, p is the number of hydroxide ion ($OH^-$) that bonds to the cation, which is an integer of 1 or more.

The slurry composition may further include ammonia and ammonium ions in addition to the precipitate and 3-hydroxypropionic acid.

Further, the slurry composition may be formed in the process of recovering 3-hydroxypropionic acid according to one embodiment of the invention, and for example, it may be formed in the step of adding ammonia to the solution containing 3-hydroxypropionate crystal.

The particle size of the precipitate may be 1.0 μm or more, 1.5 μm or more, 10.0 μm or more, 13.0 μm or more, or 15.0 μm or more, and, 300.0 μm or less, 250.0 μm or less, 200.0 μm or less, 150.0 μm or less, 100.0 μm or less, 50.0 μm or less, or 30.0 μm or less. Since the precipitate satisfies the above-mentioned particle size, filtration separation from the slurry can be made very easy. The precipitate may exhibit various particle shapes such as angular, spherical, plate-shape, and needle-shape. Further, the particle size of the precipitate can be measured by a scanning electron microscopy (SEM). At this time, the particle size of the precipitate is measured based on the straight-line distance between crystal planes with the longest distance among the straight-line distances between crystal planes contained in the precipitate.

Advantageous Effects

In the process of recovering 3-hydroxypropionic acid provided by the present invention, by-products and/or additives can be easily separated through crystallization of 3-hydroxypropionate, thereby recovering 3-hydroxypropionate with a high purity. 3-Hydroxypropionic acid can be recovered in a high purity and high yield by a step of separating the precipitate from the slurry prepared by adding ammonia to the recovery process, and the like. In addition, the precipitate can be reused as a neutralizing agent, and nitrogen-containing compounds such as ammonia recovered from the filtrate in which the precipitate has been filtered can be recycled in the fertilizer production process, etc., thereby suppressing the generation of waste and providing an environmentally friendly recovery process for 3-hydroxypropionic acid.

Hereinafter, the present invention will be described in more detail with reference to examples. However, the following examples are for illustrative purposes only, and are not intended to limit the scope of the present invention.

Preparation Example 1: Preparation of Bacterium Strain for Producing 3-Hydroxypropionic Acid Recombinant vectors into which genes encoding glycerol dehydratase and aldehyde dehydrogenase, which are known to produce 3-hydroxypropionic acid (3HP) using glycerol as a substrate, were introduced were manufactured. The prepared recombinant vector was introduced into *E. coli* W3110 strain to prepare a 3-hydroxypropionic acid-producing strain.

More specifically, a BtuR gene encoding adenosyltransferase was cloned into plasmid pCDF containing a gene (dhaB) encoding glycerol dehydratase, a gene (aldH) encoding aldehyde dehydrogenase and a gene (gdrAB) encoding glycerol dehydratase reactivase. The resulting pCDF_J23101_dhaB_gdrAB_J23100_aldH_btuR vector was introduced into strain W3110 (KCCM 40219) by an electroporation method using an electroporation device (Bio-Rad, Gene Pulser Xcell) to prepare 3-hydroxypropionic acid-producing strain. The process of preparing the 3-hydroxypropionic acid-producing strain of Preparation Example 1 and the vectors, primers, and enzymes used were carried out with reference to Example 1 of Korean Unexamined Patent Publication No. 10-2020-0051375, which is incorporated herein by reference.

Preparation Example 2: Preparation of $Mg(3HP)_2$ Crystal

The 3-hydroxypropionic acid-producing strain prepared in Preparation Example 1 was fermented and cultured at 35° C. in a 5 L fermenter using unpurified glycerol as a carbon source to produce 3-hydroxypropionic acid. In order to prevent the lowering of pH due to the production of 3-hydroxypropionic acid, magnesium hydroxide ($Mg(OH)_2$), which is an alkali metal salt, was added thereto to maintain the pH to be neutral during the fermentation.

After fermentation culture, cells were removed by centrifugation (4000 rpm, 10 minutes, 4° C.), and primary fermentation liquid purification (primary purification) was performed using activated carbon. Specifically, activated carbon was added to the fermentation liquid from which bacterial cells were removed by centrifugation, the mixture was well mixed, and then centrifuged again to separate the activated carbon. Then, the fermentation liquid from which the activated carbon was separated was filtered with a vacuum pump through a 0.7 um filter paper to purify the 3-hydroxypropionic acid fermentation liquid.

The concentration of 3-hydroxypropionic acid in the fermentation liquid after completion of the primary purification was a level of about 50 to 100 g/L, and the fermentation liquid was concentrated to a concentration of 800 g/L using a rotary evaporator (50° C., 50 mbar) to prepare a concentrate, and ethanol was added in an amount of two times the volume of the concentrate, and stirred (3000 rpm) at room temperature to produce $Mg(3HP)_2$ crystals.

At this time, the concentration of the alkali metal salt in the concentrate was 493.3 g/L (based on $Mg(OH)_2$). The resulting crystals were washed three times with ethanol (EtOH) and dried in an oven at 50° C. to finally recover the crystals.

Example 1

22.2 g of $Mg(3HP)_2$ crystal recovered in Preparation Example 2 were added to 89.1 ml of distilled water, and stirred for 20 minutes to prepare an aqueous $Mg(3HP)_2$ solution (solution A). 400 g of 28% ammonia water was added to the solution A, and stirred at room temperature in an airtight container for 20 hours to form a slurry containing $Mg(OH)_2$ precipitate and 3-hydroxypropionic acid. The slurry was then filtered using a filtration flask and a vacuum pump, and separated into the $Mg(OH)_2$ precipitate and a filtrate 1. Then, the filtered $Mg(OH)_2$ precipitate was washed with 700 ml of distilled water, the washing water was filtered to recover the filtered washing water 2. At this time, the filtrate 1 and the filtered washing water 2 were a solution B (1114 g).

Example 2

A solution B was recovered in the same manner as in Example 1. In addition, in order to remove excess ammonia contained in Solution B, 250 g of the solution B was added to a flask, and the internal pressure of the flask was reduced to 160 mbar using a vacuum pump. Then, while raising the internal temperature of the flask to 68° C., the mixture was stirred for 1 hour. Then, the flask was cooled to room temperature to recover 66.5 g of a solution C.

Example 3

A solution C was recovered in the same manner as in Example 2. In addition, zeolite (CBV2314, Zeolyst) was used to adsorb ammonium ions present in the solution C.

Specifically, the zeolite was heat-treated at a temperature of 500° C. for 5 hours in an air atmosphere to obtain zeolite from which ammonium ions have been removed. 20 g of heat-treated zeolite was then added to 40 g of the solution C and stirred at room temperature for 30 minutes. Then, filtration was performed using a filtration flask and a vacuum pump to separate a solid Y and a solution D. 20 g of heat-treated zeolite was further added to a solution D, and stirred at room temperature for 30 minutes. Then, filtration was performed using a filtration flask and a vacuum pump to separate a solid Z and a solution E.

Comparative Example 1

The 3-hydroxypropionic acid-producing strain prepared in Preparation Example 1 was fermented and cultured at 35° C. in a 5 L fermenter using unpurified glycerol as a carbon source to produce 3-hydroxypropionic acid. In order to prevent the lowering of pH due to the production of 3-hydroxypropionic acid, calcium hydroxide ($Ca(OH)_2$), which is an alkali metal salt, was added to maintain the pH to be neutral during the fermentation.

After fermentation culture, cells were removed by centrifugation (4000 rpm, 10 minutes, 4° C.), and primary fermentation liquid purification (primary purification) was performed using activated carbon. Specifically, activated carbon was added to the fermentation liquid from which bacterial cells were removed by centrifugation, the mixture was well mixed, and then centrifuged again to separate the activated carbon. Then, the fermentation liquid from which the activated carbon was separated was filtered with a vacuum pump through a 0.7 um filter paper to purify the 3-hydroxypropionic acid fermentation liquid.

The 3-hydroxypropionic acid fermentation liquid in which the concentration of 3-hydroxypropionic acid or its metal salt was 8 wt. % was added to a 2 L reactor, and then stirred.

Then, after raising the temperature to 60° C., 108 g of a 95% sulfuric acid solution (1 equivalent relative to 3HP equivalent) was added, and stirred. When $CaSO_4$ crystals were formed in the entirety of the reactor, the temperature was cooled to room temperature.

The resulting $CaSO_4$ precipitate was filtered using a 0.45 micro filter, and the remaining filtrate was concentrated to a concentration of 30 wt. % 3-hydroxypropionic acid.

The concentrate was passed through a cation exchange resin (SL-BH, Samyang Corporation) column to remove residual ionic impurities, thereby obtaining 3-hydroxypropionic acid (3HP concentration: 8 wt. %). The resulting 3-hydroxypropionic acid was concentrated (liquid F) to a concentration of 30 wt. % 3-hydroxypropionic acid.

Test Example

1. Content Analysis of Magnesium Element (Mg) and Nitrogen Element (N)

In Examples, the contents of magnesium element (Mg) and nitrogen element (N) contained in solutions (A, B, C, E) and solids (X, Y) were analyzed, and the results are shown in Table 1 below.

Specifically, the content of magnesium element (Mg) was analyzed by inductively coupled plasma optical emission spectroscopy (ICP-OES), and the content of nitrogen element (N) was measured through NSX elemental analysis (Nitrogen, Sulfur and Halogen Elemental Analysis).

2. Measurement of Recovery Rate of 3-Hydroxypropionic Acid (3HP)

In Comparative Examples, the recovery rate of 3-hydroxypropionic acid was measured by a high performance liquid chromatography (HPLC). Specifically, the content (Y) of 3-hydroxypropionic acid or a metal salt thereof contained in the strain fermentation liquid containing the 3-hydroxypropionic acid or a metal salt thereof, and the content (X) of 3-hydroxypropionic acid finally recovered were measured, and substituted into the following Equation 1 to calculate the recovery rate of 3-hydroxypropionic acid.

$$\text{Recovery of 3-hydroxypropionic acid (\%)} = X/Y*100 \quad \text{[Equation 1]}$$

3. Measurement of Impurity Content

With respect to the 3-hydroxypropionic acid obtained in Comparative Examples, the content of impurities (Ca, Na, S, Cl) was measured using inductively coupled plasma optical emission spectroscopy (ICP-OES: Optima8300DV, Perkinelmer), High-Performance Liquid Chromatography (HPLC) and 1H-NMR.

TABLE 1

| | | Magnesium element content (mmol) | Nitrogen element content (mmol) | Calcium element content (ppm) | Sodium element content (ppm) | Sulfur element content (ppm) | Chlorine element content (ppm) |
|---|---|---|---|---|---|---|---|
| Example 1 | Solution A | 81.5 | — | — | — | — | — |
| | Solution B (recovery amount; 1114 g) | 4.6 | 4533.3 | — | — | — | — |
| Example 2 | Solution B (usage amount; 250 g) | 1.0 | 1017.3 | — | — | — | — |
| | Solution C (recovery amount; 66.5 g) | 1.0 | 33.2 | — | — | — | — |
| Example 3 | Solution C (usage amount; 40 g) | 0.6 | 20.0 | — | — | — | — |
| | Solid X and Solid Y | — | 19.4 | — | — | — | — |
| | Liquid E | 0.6 | 0.6 | — | — | — | — |
| Comparative Example 1 | Liquid F | — | — | 200 | 1000 | 1000 | 1000 |

Referring to Table 1, it was confirmed that since the content of magnesium element (Mg) in the solution B in Example 1 was 5.6 wt. % with respect to 100 wt. % of the magnesium element (Mg) content contained in the solution A, 94.4 wt. % of magnesium element was removed by the formation and filtration of $Mg(OH)_2$ precipitate.

In addition, it was confirmed that since the content of nitrogen element (N) contained in the solution C in Example 2 was 3.3 wt. % with respect to 100 wt. % of the nitrogen element (N) content contained in the solution B, 96.7 wt. % of the nitrogen element was removed by stripping ammonia. Furthermore, in Example 3, the total content of nitrogen element (N) contained in solids X and Y was 97 wt. % with respect to 100 wt. % of the nitrogen element (N) content contained in solution C, 97 wt. % of nitrogen was removed by zeolite adsorption. Accordingly, it was confirmed that the total content of nitrogen elements removed in Examples 2 and 3 was 99.9 wt. % (={100 wt. %−(3.3 wt. %×3 wt. %)}).

Therefore, the removal rate of cations removed by Examples 1 to 3 and the recovery rate of 3-hydroxypropionic acid were 94.4 wt. % in total (=94.4 wt. %×99.9 wt. %).

On the other hand, it was confirmed that the recovery rate of 3-hydroxypropionic acid in Comparative Example 1 was 90%, which was lower than that of Examples 1 to 3, and even after purification, impurities of calcium, sodium, sulfur and chlorine elements were contained in a large amount.

What is claimed is:

1. A process of recovering 3-hydroxypropionic acid, comprising:

forming a 3-hydroxypropionate crystal in a concentrate containing 3-hydroxypropionic acid in the presence of an alkali metal salt;

preparing a solution containing the 3-hydroxypropionate crystal separated from the concentrate; and adding ammonia to the solution containing the 3-hydroxypropionate crystal.

2. The process of recovering 3-hydroxypropionic acid according to claim 1, wherein:

a slurry composition containing a precipitate represented by the following structural formula 3 is formed during the adding ammonia to the solution containing the 3-hydroxypropionate crystal;

$Cation(OH)_p$ [Structural Formula 3 wherein,

Cation is a cation of the alkali metal salt, and p is the number of a hydroxide ion ($OH^-$) that binds to the cation, which is an integer of 1 or more.

3. The process of recovering 3-hydroxypropionic acid according to claim 2, further comprising:

filtering the slurry composition to recover a filtrate, and stripping ammonia from the filtrate under a reduced pressure condition.

4. The process of recovering 3-hydroxypropionic acid according to claim 3, further comprising:

adding an adsorbent to the filtrate from which the ammonia has been removed to adsorb ammonium ions.

5. The process of recovering 3-hydroxypropionic acid according to claim 4, wherein:

the adsorbent is at least one selected from the group consisting of zeolite, activated carbon, silica gel, and alumina gel.

6. The process of recovering 3-hydroxypropionic acid according to claim 1, wherein:

the concentrate contains at least 300 g/L of the 3-hydroxypropionic acid.

7. The process of recovering 3-hydroxypropionic acid according to claim 1, wherein:

the concentrate contains 350 g/L or more and 900 g/L or less of the 3-hydroxypropionic acid.

8. The process of recovering 3-hydroxypropionic acid according to claim 1, wherein:

the 3-hydroxypropionate crystal is represented by the following structural formula 1 or structural formula 2:

Cation(3HP)n [Structural Formula 1]

$Cation(3HP)n \cdot mH_2O$ [Structural Formula 2]

wherein,

Cation is a cation of the alkali metal salt,

3HP is 3-hydroxypropionic acid that binds to the cation, n is the number of 3HP that binds to the cation, which is an integer of 1 or more, and m is the number of water molecules in the hydrate, which is an integer of 1 or more.

9. The process of recovering 3-hydroxypropionic acid according to claim 1, wherein:

the alkali metal salt is $Ca(OH)_2$, $Mg(OH)_2$ or a mixture thereof.

10. The process of recovering 3-hydroxypropionic acid according to claim 1, wherein:

the 3-hydroxypropionate crystal has a particle size distribution $D_{50}$ of 20 μm or more and 90 μm or less, and $(D_{90}-D_{10})/D_{50}$ of 1.00 or more and 3.00 or less.

11. The process of recovering 3-hydroxypropionic acid according to claim 1, wherein:

the solution containing the 3-hydroxypropionate crystal contains 100 g/L or more and 800 g/L or less of the 3-hydroxypropionate crystal.

12. The process of recovering 3-hydroxypropionic acid according to claim 1, further comprising:

fermenting a bacterium strain having 3-hydroxypropionic acid-producing ability to produce a 3-hydroxypropionic acid fermentation liquid; and concentrating the fermentation liquid to form the concentrate containing 3-hydroxypropionic acid.

13. The process of recovering 3-hydroxypropionic acid according to claim 1, wherein:

a recovery rate of 3-hydroxypropionic acid is at least 40%.

14. A 3-hydroxypropionic acid-containing slurry composition, comprising a precipitate represented by the following structural formula 4 and 3-hydroxypropionic acid:

$Cation(OH)_p$ [Structural Formula 4]

wherein,

Cation is $Mg^{2+}$ or $Ca^{2+}$, and p is the number of hydroxide ion ($OH^-$) that binds to the cation, which is an integer of 1 or more.

15. The slurry composition according to claim 14, further comprising ammonia and ammonium ions.

* * * * *